(12) United States Patent
Hasegawa

(10) Patent No.: US 7,554,245 B2
(45) Date of Patent: Jun. 30, 2009

(54) ULTRASONIC PROBE

(75) Inventor: Yasunobu Hasegawa, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 624 days.

(21) Appl. No.: 11/449,544

(22) Filed: Jun. 8, 2006

(65) Prior Publication Data

US 2006/0284086 A1    Dec. 21, 2006

(30) Foreign Application Priority Data

Jun. 15, 2005    (JP) .............................. 2005-175700

(51) Int. Cl.
*H01L 41/00* (2006.01)
(52) U.S. Cl. ...................... 310/334; 310/335; 310/336; 600/459
(58) Field of Classification Search ....... 250/306–443.1
See application file for complete search history.

(56) References Cited

U.S. PATENT DOCUMENTS

| | | | | |
|---|---|---|---|---|
| 4,494,548 A | * | 1/1985 | Buon et al. | 600/446 |
| 5,377,682 A | * | 1/1995 | Ueno et al. | 600/446 |
| 6,020,675 A | * | 2/2000 | Yamashita et al. | 310/358 |
| 6,813,950 B2 | * | 11/2004 | Glascock et al. | 73/633 |

FOREIGN PATENT DOCUMENTS

| | | |
|---|---|---|
| JP | 7-38851 | 5/1995 |
| JP | 2003-175033 | 6/2003 |
| JP | 2003175033 A * | 6/2003 |

OTHER PUBLICATIONS

Office Action issued Nov. 21, 2008 of the corresponding Chinese Patent Application No. 200610092240.4.

* cited by examiner

*Primary Examiner*—David A Vanore
*Assistant Examiner*—Andrew Smyth
(74) *Attorney, Agent, or Firm*—Scott D. Wofsy; Edwards Angell Palmer & Dodge LLP

(57) ABSTRACT

The invention relates to an oscillating ultrasonic probe that comprises a group of piezoelectric elements consisting of a plurality of narrow card-shaped piezoelectric elements arrayed in a long-axis direction and connecting wires such as a flexible substrate which are connected electrically to those piezoelectric elements and which extends outward from at least one end side in a short-axis direction; a rotational mechanism portion that causes the group of piezoelectric elements to rotate and oscillate to left and right in the short-axis direction about the center of the long-axis direction; a reference position detection sensor that detects a reference position in the short-axis direction of the group of piezoelectric elements; and a control shaft and a stepping motor linked to the reference position detection sensor and driving the rotational mechanism portion; wherein an optical rotary plate for the reference position sensor, which has a boundary region between a light-blocking portion and a light-transmitting portion, is linked to the control shaft; a light-blocking portion and a light-transmitting portion are formed sequentially at a predetermined angle in mutually opposite directions from the center of the optical rotary plate, with reference to a boundary region, and also the optical rotary plate rotates no further than a predetermined angle with reference to the boundary region. This configuration simplifies the mechanism for detecting the rotational angle of the group of piezoelectric elements, simplifies the detection of the reference position, and prevents damage to the flexible substrate.

5 Claims, 8 Drawing Sheets ered as an optical encoder (see FIG. 6) and consists of an
ULTRASONIC PROBE

BACKGROUND OF THE INVENTION

1. Field of the Invention

The present invention relates to an ultrasonic probe in which a group of piezoelectric elements oscillates in the short-axis direction of the probe to obtain a three-dimensional image (hereinafter called a "short-axis oscillating probe") and, in particular, to a short-axis oscillating probe of a simple configuration that uses a stepping motor.

2. Description of Related Art

A short-axis oscillating probe that is known in the art obtains a three-dimensional image by electronically scanning a group of piezoelectric elements in the long-axis direction of the probe and also by mechanically scanning (oscillating) the group of piezoelectric elements in that short-axis direction (see Japanese Patent Publication No. 7-38851 and Japanese Patent Laid-Open Publication No. 2003-175033). Since components such as wiring (connective wires) and scan circuitry of this type of short-axis oscillating probe can be configured simply, in comparison with a matrix type of probe in which piezoelectric elements are arrayed horizontally and vertically to provide a two-dimensional scan, this probe can be implemented easily.

A prior-art example of a short-axis oscillating probe (see Japanese Patent Publication No. 7-38851) is shown in FIG. 5A, where FIG. 5A is a section taken along the long-axis direction (X-X direction) of the probe and FIG. 5B is a section taken along the short-axis direction (Y-Y direction) thereof.

This prior-art short-axis oscillating probe is provided with a group of piezoelectric elements 101, a rotational mechanism portion 102, and a rotational angle detection mechanism 103. The group of piezoelectric elements 101 is arrayed on a base 104 to which backing material is attached, with the widthwise direction of the plurality of narrow card-shaped piezoelectric elements 101a aligned in the long-axis direction and also the lengthwise direction thereof aligned in the short-axis direction. This backing material is affixed on top of the base 104, which is formed of a plastic material in a convex dome shape in the long-axis direction, with the configuration being such that the group of piezoelectric elements 101 is curved outward in the long-axis direction.

A flexible substrate 105 that has been connected electrically to the group of piezoelectric elements 101 over the entire region of the probe in the long-axis direction thereof is lead out downward from one end side of the probe in the short-axis direction, as shown in FIG. 5B. In this case, a conductive path 105a of the flexible substrate 105 is connected electrically to a drive electrode of each piezoelectric element 101a.

The rotational mechanism portion 102 shown in FIG. 5A is formed of a retaining plate 106 of a metal material, a case 107, a segment-shaped first bevel gear 108a, a second bevel gear 108b, a control shaft 109, and a stepping motor 110. The retaining plate 106 has leg portions 106a and 106b on the lower surface thereof on both edge sides in the long-axis direction, and the base 104 holding the group of piezoelectric elements 101 consisting of the plurality of piezoelectric elements 101a is affixed to the upper surface thereof. In the leg portions 106a and 106b, center shafts 111a and 111b that penetrate through the leg portions 106a and 106b are supported in rotation by bearings 111c and 111d in the long-axis direction (on the line X-X in the horizontal direction of the case 107), with the leg portions 106a and 106b being provided to be freely rotatable about the center shafts 111a and 111b.

The case 107 is formed to be concave in section with the upper surface thereof being open, and projecting ends of the center shafts 111a and 111b that bear the leg portions 106a and 106b are affixed to peripheral walls of the case 107. A slit 112 is formed in the long-axis direction of the bottom wall of the case 107, as shown in FIG. 5B, and the flexible substrate 105 that is connected to the group of piezoelectric elements 101 is lead out to the exterior of the case 107 therethrough. A material such as a plastic material is embedding in the slit 112 to seal the same.

The first bevel gear 108a of a segment shape is affixed by screws or the like to the inner surface of the leg portion 106a that is one of the leg portions provided on the retaining plate 106, below the center shaft 111a that passes therethrough and is supported in rotation thereby, and has teeth in an arc (a fan shape) with a peak thereof at the lower end in the vertical direction. The second bevel gear 108b is supported rotatably on the free end of the control shaft 109 that is aligned in the vertical direction perpendicular to the center shafts 111a and 111b (the line X-X), engages with the first bevel gear 108a, and rotates in the horizontal direction. The control shaft 109 is lead out of the case 107 from the bottom wall of the case 107 and is sealed by a bearing seal member 114, and the other end thereof is linked to the stepping motor 110 by means such as a gear linkage.

The rotational angle detection mechanism 103 is configured as an optical encoder (see FIG. 6) and consists of an optical rotary plate 103a, which is integral with the control shaft 109, and an optical counter 103b, which is U-shaped in section and into which the outer periphery of the optical rotary plate 103a is inserted. A large number of small holes 103c are provided around the outer periphery of the optical rotary plate 103a, and the optical counter 103b has a light-emitting portion and a light-receiving portion on leg portions that face the optical rotary plate 103a.

Light that has been transmitted through one of a number of small holes 103c from the light-emitting portion of the optical counter 103b is detected by the light-receiving portion, and the reference position of the group of piezoelectric elements 101 is detected by counting the number of times that light is transmitted therethrough. This reference position is positioned on the centerline that bisects the short-axis direction, by way of example, and is detected by means of a number of optical or magnetic sensors. Note that a cover that encloses the group of piezoelectric elements 101 is provided for the case 107, the group of piezoelectric elements 101 and other components are hermetically sealed therein, and the interior thereof is filled with an ultrasound transmission medium such as oil.

In the thus-configured probe of the prior art, the rotation of the second bevel gear 108b of the rotational mechanism portion 102 horizontally to left and right causes the first bevel gear 108a that is engaged therewith to rotate and oscillate with respect to the vertical plane so that the peak thereof inclines upward to the left or right from the center. In other words, the peak of the first bevel gear 108a rotates and oscillates to the left and right of the vertical direction acting as center. Thus the leg portions 106a and 106b of the retaining plate 106 rotate and oscillate to the left and right with respect to the center shafts 111a and 111b, and also the group of piezoelectric elements 101 rotate and oscillate to the left and right in the short-axis direction, in the opposite directions thereto. In addition, the rotational angle of the group of piezoelectric elements 101 in the short-axis direction is detected by the rotational angle detection mechanism 103, ensuring that biological information is obtained from precise positions of the object to be detected (organism).

Problems with Prior Art

However, the prior-art short-axis oscillating probe of this configuration has a problem in that it is complicated both mechanically and structurally and thus is expensive, since the rotational angle in the short-axis direction from the reference position of the group of piezoelectric elements 101 is detected by an optical encoder that is the rotational angle detection mechanism 103.

For that reason, the prior-art probe disclosed in Japanese Patent Laid-Open Publication No. 2003-175033 has a configuration in which the drive motor 110 shown in FIG. 5A is a stepping motor that is rotated intermittently by pulses, and the rotational angle is detected by counting the number of pulses from the reference position of the group of piezoelectric elements 101, making an optical encoder unnecessary.

In this prior-art probe, a magnet 115a is provided in the center of the group of piezoelectric elements 101 in the short-axis direction thereof, as shown in FIG. 7A, and the reference position of the group of piezoelectric elements 101 is detected by the mutual operation of the magnet 115a with a Hall sensor 115b provided in the center of a case 107a of the probe. In other words, the reference position of the group of piezoelectric elements 101 is taken as the point at which a centerline OP that bisects the short-axis direction from a center of rotation O coincides with the center of the cover 107a, as shown in FIG. 7A. More specifically, this reference position is taken as being where the center of the group of piezoelectric elements 101 in the short-axis direction lies on the centerline OP that bisects the rotational angle through which the group of piezoelectric elements 101 oscillates by rotating to the left and right. The reference position is detected by the reference position detection sensor that is configured of a magnetic sensor therefor.

If the group of piezoelectric elements 101 rotates through an angle θ° to the right at the start of operation of this short-axis oscillating probe of the prior art as shown in FIG. 7B, however, it is not clear whether the direction of "shift" (on a centerline OP') is to the left or the right, and thus the direction of rotation of the group of piezoelectric elements 101 that is used for determining the reference position is also unclear. This raises a problem in that it becomes extremely difficult to detect and set the reference position.

In addition, since the group of piezoelectric elements 101 rotates and oscillates in the short-axis direction of this prior-art probe, the flexible substrate 105 that extends outward from the group of piezoelectric elements 101 is sealed into and accommodated by the case 107 while retaining the flexibility thereof. For that reason, there is a danger that the flexible substrate 105 will come into contact with the components of the rotational mechanism portion 102, particularly the first bevel gear 108a, and the flexible substrate 105 will sustain damage such as breakage of the conductive path 105a thereof.

A first objective of the present invention is to simplify the mechanism for detecting the rotational angle of the group of piezoelectric elements in the short-axis oscillating probe, and a second objective thereof is to prevent damage to the flexible substrate.

SUMMARY OF THE INVENTION

In order to achieve the abovementioned first objective, the present invention relates to an ultrasonic probe comprising: a group of piezoelectric elements consisting of a plurality of piezoelectric elements of a narrow card shape arrayed in a long-axis direction of the probe and also connecting wires connected electrically to the piezoelectric elements and extending outward from at least one end side in a short-axis direction of the probe; a rotational mechanism portion that rotates and oscillates the group of piezoelectric elements in the short-axis direction about the center of the long-axis direction; a reference position detection sensor that detects a reference position in the short-axis direction of the group of piezoelectric elements; and a control shaft and a stepping motor linked to the reference position sensor and driving the rotational mechanism portion; wherein an optical rotary plate for the reference position sensor, which has a boundary region between a light-blocking portion and a light-transmitting portion, is linked to the control shaft; the light-blocking portion and the light-transmitting portion are formed sequentially at a predetermined angle in mutually opposite directions from the center of the optical rotary plate, with reference to a boundary region, and also the optical rotary plate rotates no further than a predetermined angle with reference to the boundary region; the boundary region is detected by the transmission or blocking of light by the light-blocking portion and the light-transmitting portion; and the reference position of the group of piezoelectric elements is set on the basis of the thus-detected boundary region.

In order to achieve the abovementioned second objective, the present invention relates to an ultrasonic probe having at least: a group of piezoelectric elements consisting of a plurality of piezoelectric elements of a narrow card shape arrayed in a long-axis direction and also connecting wires such as a flexible substrate connected electrically to the piezoelectric elements and extending outward from at least one end side in a short-axis direction of the probe; a rotational mechanism portion that rotates and oscillates the group of piezoelectric elements in the short-axis direction about the center of the long-axis direction; a reference position detection sensor that detects a reference position in the short-axis direction of the group of piezoelectric elements; and a stepping motor linked to the reference position sensor that drives the rotational mechanism portion; wherein the rotational mechanism portion is provided with a retaining plate that supports the group of piezoelectric elements on an upper surface thereof and has a leg portion on each side of a lower surface in the long-axis direction; a case of concave shape in which the leg portions connected to a peripheral wall thereof on either side of a line linking the two leg portions are freely rotatable and within which the flexible substrate is sealed and is lead out to the exterior through a bottom wall thereof; a first bevel gear affixed to one inner surface of the leg portions and having teeth in an arc shape; a second bevel gear engaging with the first bevel gear and rotating in the horizontal plane; and a control shaft that rotatably supports the second bevel gear that is driven in rotation by the drive motor and that is also sealed from the bottom wall and is lead out therefrom; and wherein a protective cover that covers the second bevel gear is affixed to the bottom wall to prevent contact by the flexible substrate on the second bevel gear.

The present invention enables detection of the boundary region of the optical rotary plated linked to the control shaft, to enable simple detection and setting of the reference of the group of piezoelectric elements. This enables a simple grasping of the position (rotational angle) in the short-axis direction of the group of piezoelectric elements from the reference position, by counting the number of pulsed generated by transmitting or blocking light by the optical rotary plate that is rotated by the stepping motor. This enables a simplification of the detection mechanism in the short-axis direction of the group of piezoelectric elements.

In accordance with the present invention, the optical rotary plate that acts as the reference position sensor has a light-blocking portion and a light-transmitting portion that are sequential in mutually opposite directions from the boundary region, and also this optical rotary plate rotates no further than a predetermined angle with reference to that boundary region. Since only one point of the boundary region is encountered during the rotation of the optical rotary plate, the boundary region that defines the reference position can be detected reliably.

Even if the group of piezoelectric elements is "shifted" in either direction (right or left) from the reference position at the start of operation of the reference position sensor, the direction of that "shift" can be reliably sensed because there is a light-blocking portion and a light-transmitting portion on either side of the boundary region of the optical rotary plate that corresponds to the reference position. Therefore, since the optical rotary plate can be rotated toward the light-blocking side if the "shift" is toward the light-transmission side, or towards the light-transmission side if the "shift" is toward the light-blocking side, by way of example, the reference position for the group of piezoelectric elements can be detected simply and thus the reference position of the group of piezoelectric elements can be set simply.

Furthermore, it is possible to avoid damage to the flexible substrate and particularly breakage of the conductive path thereof because the protective cover, which prevents contact between the flexible substrate and the second bevel gear in accordance with this invention, covers the second bevel gear.

The rotational drive portion is not limited to a stepping motor; similar effects can be obtained with any of various other types of motor.

BRIEF DESCRIPTION OF THE DRAWINGS

FIG. 1 is illustrative of an embodying example of the short-axis oscillating probe of the present invention, where

FIG. 2 shows the reference position detection sensor of the prove of the present invention, where

FIG. 3 is illustrative of the operation of the embodying example of the probe of the present invention, where

FIG. 4 is sectional views illustrating the reference position detection sensor of the present invention, where

FIG. 5 is illustrative of the group of piezoelectric elements and the rotational mechanism portion of a prior-art example of a short-axis oscillating probe, where

FIG. 7 is sectional views illustrating the reference position detection sensor of the prior-art example, where

DETAILED DESCRIPTION OF PREFERRED EMBODIMENTS

Figure 1A:
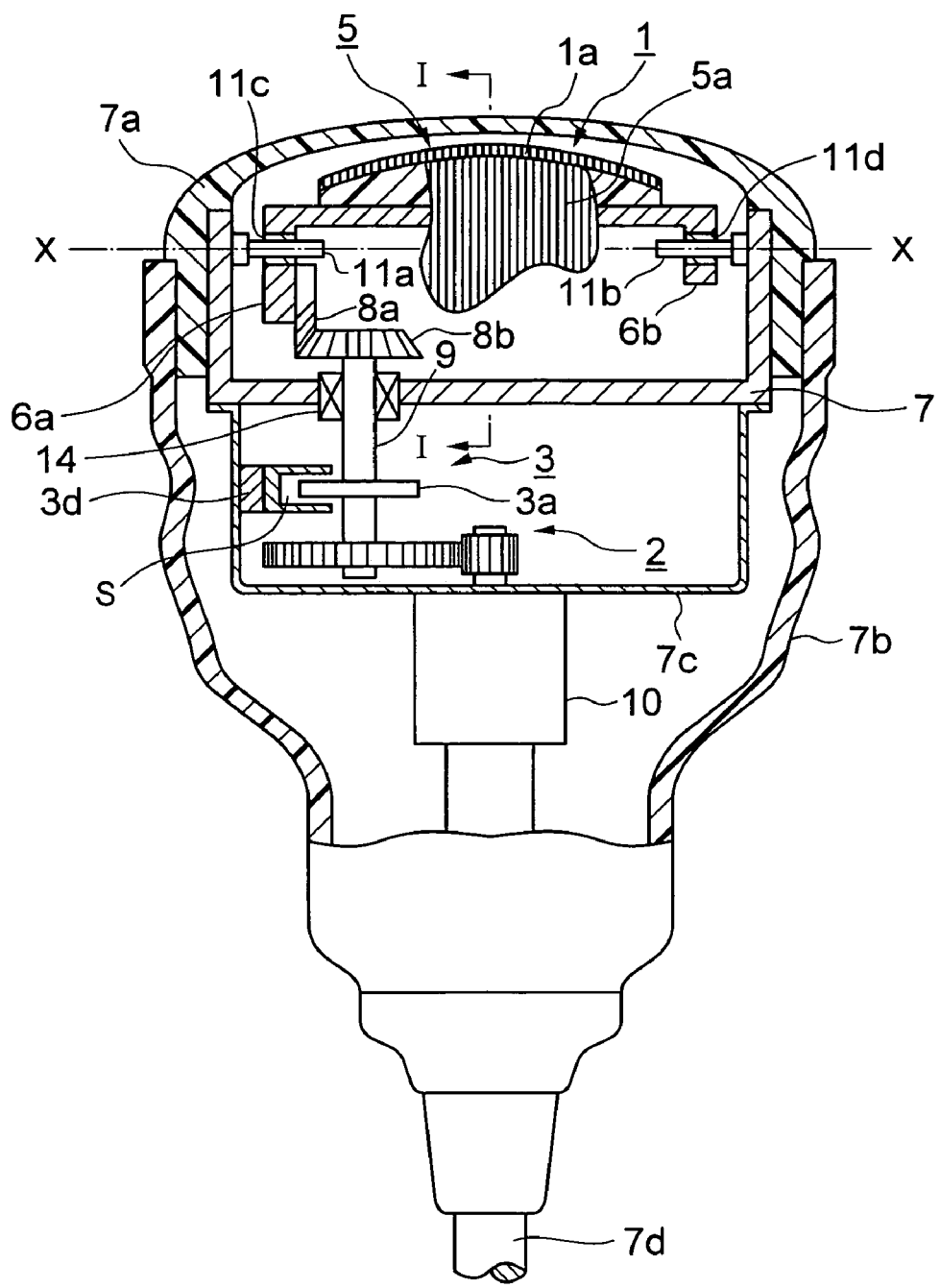
FIG. 1A is a partially cutaway longitudinal section in the long-axis direction of the short-axis oscillating probe and FIG. 1B is a lateral section in the short-axis direction of the probe of the present invention, showing the group of piezoelectric elements and the rotational mechanism portion thereof in particular.
Figure 1B:
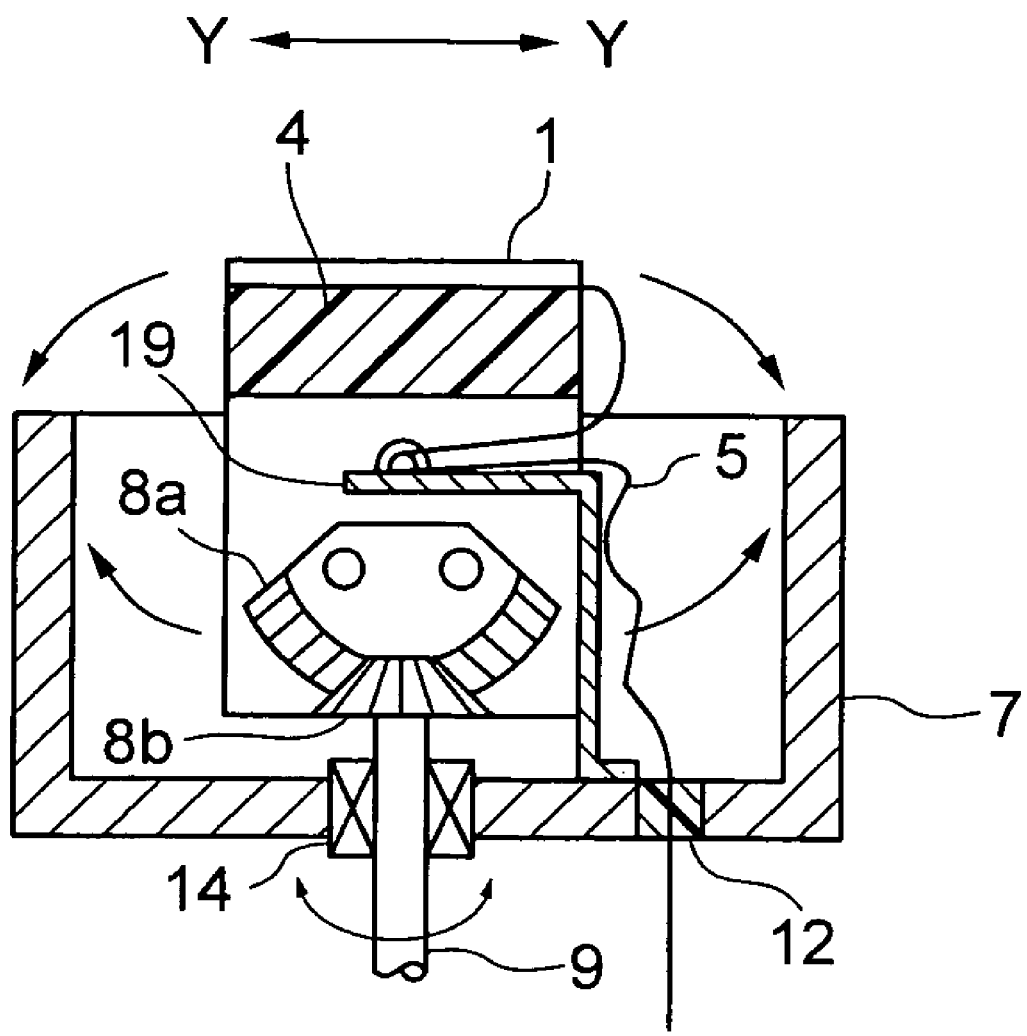

An embodying example of a short-axis oscillating probe in accordance with the present invention is shown in FIGS. 1A and 1B, where FIG. 1A is a partially cutaway section taken in the long-axis direction (X-X direction) of a short-axis oscillating probe having a rotational angle detection mechanism (reference position detection sensor) and FIG. 1B is a lateral section taken in the short-axis direction (Y-Y direction) of the rotational mechanism portion of the probe.

The short-axis oscillating probe of the present invention has a group of piezoelectric elements 1 consisting of a plurality of narrow card-shaped piezoelectric elements 1a arrayed in the long-axis direction of the probe (the X-X direction in FIG. 1A), with connecting wires such as a flexible substrate 5 extending outward therefrom, and a rotational mechanism portion 2 that rotates and oscillates in the short-axis direction thereof (in the Y-Y direction shown in FIG. 1B, perpendicular to the same plane that includes the X-X direction). In this case, a drive motor is configured as a stepping motor 10 that rotates intermittently in answer to pulses, and is provided with a reference position detection sensor 3 on a control shaft 9 thereof. Note that the stepping motor 10 is attached to a frame member 7c that is affixed to a case 7, which will be described later, and power is supplied to the stepping motor 10 and the group of piezoelectric elements 1 through a power cable 7d.

In other words, the short-axis oscillating probe of the present invention is provided with the group of piezoelectric elements 1, the rotational mechanism portion 2, and the rotational angle detection mechanism (reference position detection sensor) 3, in a similar manner to the probe of the prior art. The group of piezoelectric elements 1 is arrayed on a base 4 to which backing material is attached, with the widthwise direction of the plurality of narrow card-shaped piezoelectric elements 1a aligned in the long-axis direction and also the lengthwise direction thereof aligned in the short-axis direction. This backing material is affixed on top of the base 4, which is formed of a plastic material in a convex dome shape in the long-axis direction, with the configuration being such that the group of piezoelectric elements 1 is curved outward in the long-axis direction.

The flexible substrate 5 that has been connected electrically to the group of piezoelectric elements 1 over the entire region of the probe in the long-axis direction thereof depends from and is lead out downward from one end side of the probe in the short-axis direction, as shown in FIG. 1B. In this case, a conductive path 5a of the flexible substrate 5 is connected electrically to a drive electrode of each of the plurality of narrow card-shaped piezoelectric elements 1a. The flexible substrate 5 shown in FIGS. 1A and 1B could either be connected directly to the piezoelectric elements 1a or it could be connected indirectly thereto by means such as silver foil and conductive wiring between the drive electrodes thereof and the conductive path 5a.

The rotational mechanism portion 2 shown in FIGS. 1A and 1B is formed of a retaining plate 6 of a metal material, the case 7, a segment-shaped first bevel gear 8a, a second bevel gear 8b, the control shaft 9, and the stepping motor 10. The retaining plate 6 has leg portions 6a and 6b on the lower surface thereof on both edge sides in the long-axis direction, and the base 4 holding the group of piezoelectric elements 1 consisting of the plurality of piezoelectric elements 1a is affixed to the upper surface thereof. In the leg portions 6a and 6b, center shafts 11a and 11b that penetrate through the leg portions 6a and 6b are supported in rotation by bearings 11c and 11d in the long-axis direction (on the line X-X in the horizontal direction of the case 7), with the leg portions 6a and 6b being provided to be freely rotatable about the center shafts 11a and 11b.

The case 7 is formed to be concave in section with the upper surface thereof being open, and projecting ends of the center shafts 11a and 11b that bear the leg portions 6a and 6b are affixed to peripheral walls of the case 7. A slit 12 is formed in the long-axis direction of the bottom wall of the case 7, as shown in FIG. 1B, and the flexible substrate 5 that is connected to the group of piezoelectric elements 1 is lead out to the exterior of the case 7 therethrough. A material such as a plastic material is embedding in the slit 12 to seal the same.

The first bevel gear 8a of a segment shape is affixed by screws or the like to the inner surface of the leg portion 6a that is one of the leg portions provided on the retaining plate 6, below the center shaft 11a that passes therethrough and is supported in rotation thereby, and has teeth in an arc (a fan shape) with a peak thereof at the lower end in the vertical direction. The second bevel gear 8b is supported rotatably on the free end of the control shaft 9 that is aligned in the line Y-Y perpendicular to the center shafts 11a and 11b (the line X-X), engages with the first bevel gear 8a, and rotates in the horizontal direction. The control shaft 9 is lead out of the case 7 from the bottom wall of the case 7 and is sealed by a bearing seal member 14, and the other end thereof is linked to the stepping motor 10 by means such as a gear linkage.

Note that a cover 7a that encloses the group of piezoelectric elements 1 is provided for the case 7, the group of piezoelectric elements 1 and other components are hermetically sealed therein, the interior thereof is filled with an ultrasound transmission medium such as oil, and a housing 7b that accommodates the rotational mechanism portion 2 is engaged with the cover 7a.

In the thus-configured probe of the present invention, the rotation of the second bevel gear 8b of the rotational mechanism portion 2 horizontally to left and right causes the first bevel gear 8a that is engaged therewith to oscillate with respect to the vertical plane so that the peak thereof inclines upward to the left or right from the center. In other words, the peak of the first bevel gear 8a oscillates to the left and right of the vertical direction acting as center. Thus the leg portions 6a and 6b of the retaining plate 6 rotate and oscillate to the left and right with respect to the center shafts 11a and 11b, and also the group of piezoelectric elements 1 rotate and oscillate to the left and right in the short-axis direction, in the opposite directions thereto. This ensures that the rotational angle of the group of piezoelectric elements 1 in the short-axis direction is detected by the rotational angle detection mechanism 3, so that biological information can be obtained from precise positions of the object to be detected (organism).

Figure 2A:
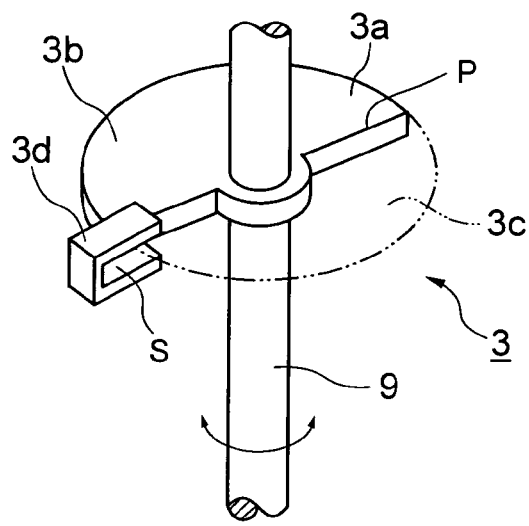
FIG. 2A is a perspective view of an embodying example in which the optical rotary plate thereof has a semicircular shape and FIG. 2B is a perspective view of an embodying example in which the optical rotary plate thereof is provided with a slit of a semicircular shape as a light-transmission portion.

The reference position detection sensor 3 is formed of an optical rotary plate 3a that is linked integrally to the control shaft 9 and a light detector 3d having a light-receiving portion of a U-shaped section, as shown in FIGS. 1A and 2A. The optical rotary plate 3a is formed of a light-blocking portion 3b and a light-transmitting portion 3c (the region indicated by a broken line in FIG. 2A) of a semicircular (half-moon) shape, and has a boundary region P formed of a linear angular position between the two. The light-blocking portion 3b and the light-transmitting portion 3c are formed sequentially to extend over 180° in mutually opposite directions from the center of rotation of the optical rotary plate 3a, with reference to the boundary region P.

The configuration is also such that the rotation and oscillation of the optical rotary plate 3a shown in FIG. 2A is controlled within 180° in mutually opposite directions with reference to the boundary region P. In this case, the control is such that rotation is within an angle of 90° in mutually opposite directions. This angular control depends on the rotation of the control shaft 9 that is linked by gears to the stepping motor 10. The light detector 3d is affixed by clasping means such as screws to the frame member 7c with shims or the like therebetween, and an outer peripheral portion of the optical rotary plate 3a is inserted into a spatial portion S of the light detector (of U-shaped section) on the outer periphery of the optical rotary plate 3a.

In this case, the initial position (reference position) of the optical rotary plate 3a is such that the boundary region P is located within the spatial portion S of the U-shaped portion of the light detector 3d, which is assumed to be the switchover point (on or off) between transmission and non-transmission of the light between the light-emitting and light-receiving portions of the light detector 3d. In this case, the group of piezoelectric elements 1 is disposed such that the centerline OP that bisects the short-axis direction from the center of rotation O is disposed on the reference position that coincides with the center of the cover 7a, in other words, the center front.

In addition, a protective cover 19 of an L-shaped section is affixed to the inner bottom surface of the case 7 of the present invention, in a configuration that covers the second bevel gear 8b, as shown in FIG. 1B. The flexible substrate 5 that extends outward from one end side of the group of piezoelectric elements 1 in the short-axis direction is folded back on itself flexible, then is led out to the exterior from the slit 12 formed in the case 7, with that portion being sealed.

Figure 3A:
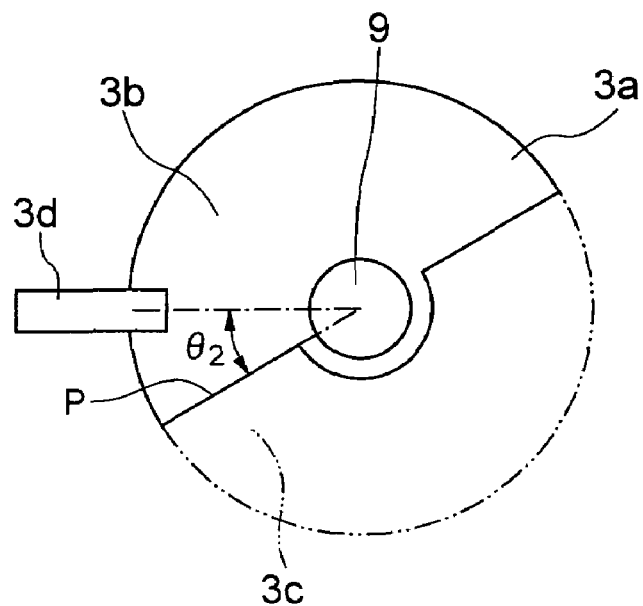
FIG. 3A is a plan view of a state in which the optical rotary plate of the reference position detection sensor has blocked the light detector (non-light-transmission state) and FIG. 3B is a plan view of a state in which the optical rotary plate does not block the light detector (light-transmission state)

In the thus-configured short-axis oscillating probe of the present invention, the operation of the short-axis oscillating probe is started by pressing a start button (not shown in the figures). In this case, assume that the boundary region P of the optical rotary plate 3a is rotated to within 90° (θ2) counterclockwise from the reference position before the start of operation of the probe, as shown by way of example in FIG. 3A, so that the light-blocking portion 3b is positioned in the spatial portion S of the light detector 3b. When the start button (not shown in the figures) is pressed in this case, the light detector 3d first catches the fact that the light-blocking portion 3b is present and detects a blocked signal. Based on this blocked signal, the stepping motor 10 is driven to rotate the optical rotary plate 3a clockwise. The boundary region P of the optical rotary plate 3a that forms the boundary between the blocking or transmission of light is then detected. The stepping motor 10 is then stopped to set the reference position.

Figure 3B:
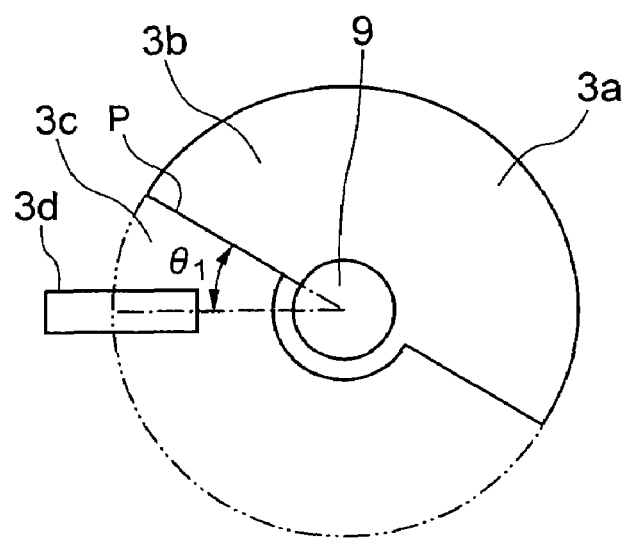

Similarly, assume that the boundary region P of the optical rotary plate 3a is rotated to within 90° (θ1) clockwise from the reference position before the start of operation of the probe, as shown by way of example in FIG. 3B, so that the light-transmitting portion 3c is positioned in the spatial portion S of the light detector 3d. In that case, the pressing of the start button first causes the light detector 3d to detect the transmission signal. Based on this transmission signal, the stepping motor 10 is driven to rotate the optical rotary plate 3a counterclockwise. In a similar manner, the boundary region P is set as the reference position.

Figure 4A:
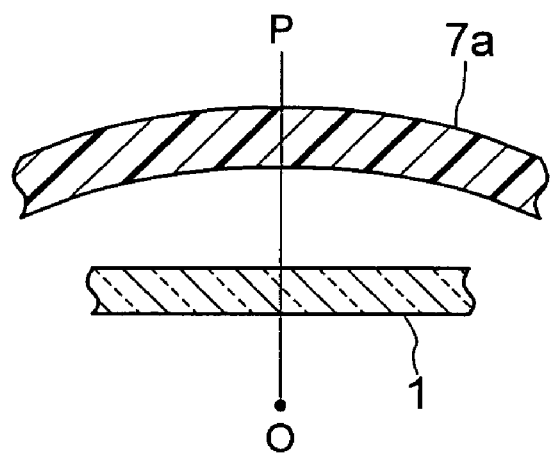
FIG. 4A shows a state in which the group of piezoelectric elements is at the reference position and FIG. 4B shows a state in which the group of piezoelectric elements 1 has rotated through θ° from the reference position.
Figure 4B:
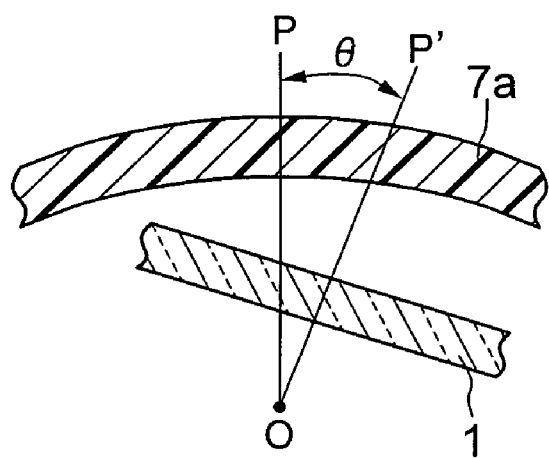
Figure 5A:
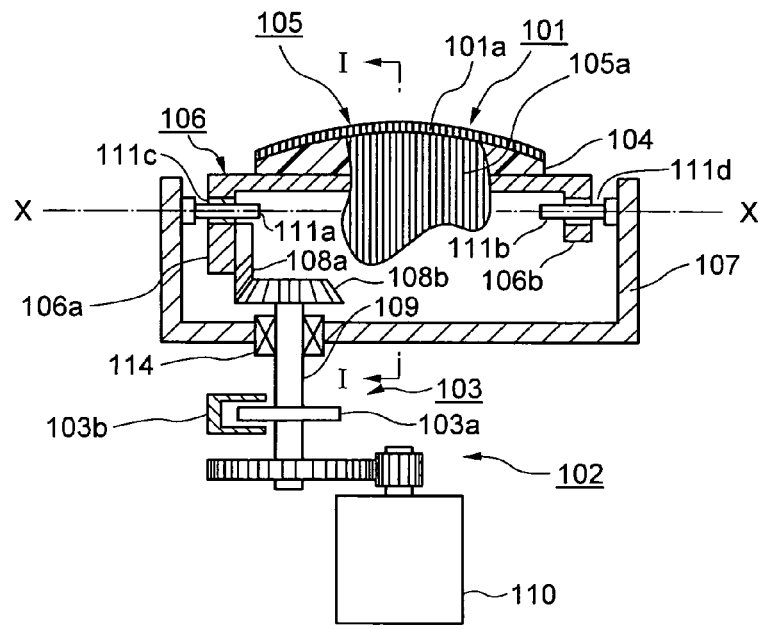
FIG. 5A is a section taken along the long-axis direction thereof and FIG. 5B is a section taken along the short-axis direction thereof.
Figure 5B:
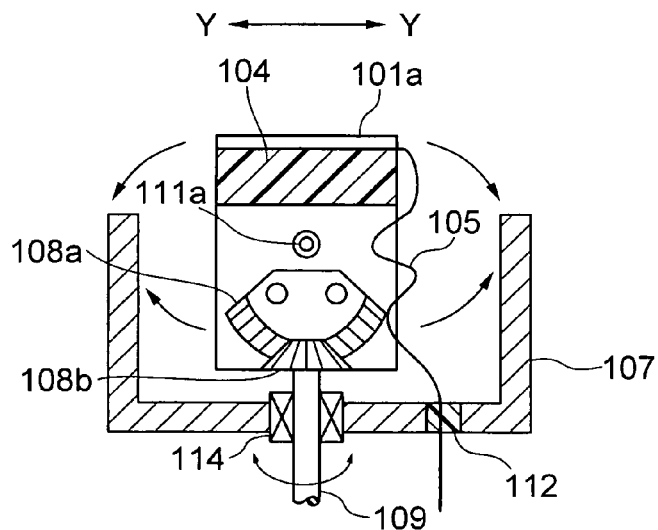
Figure 6:
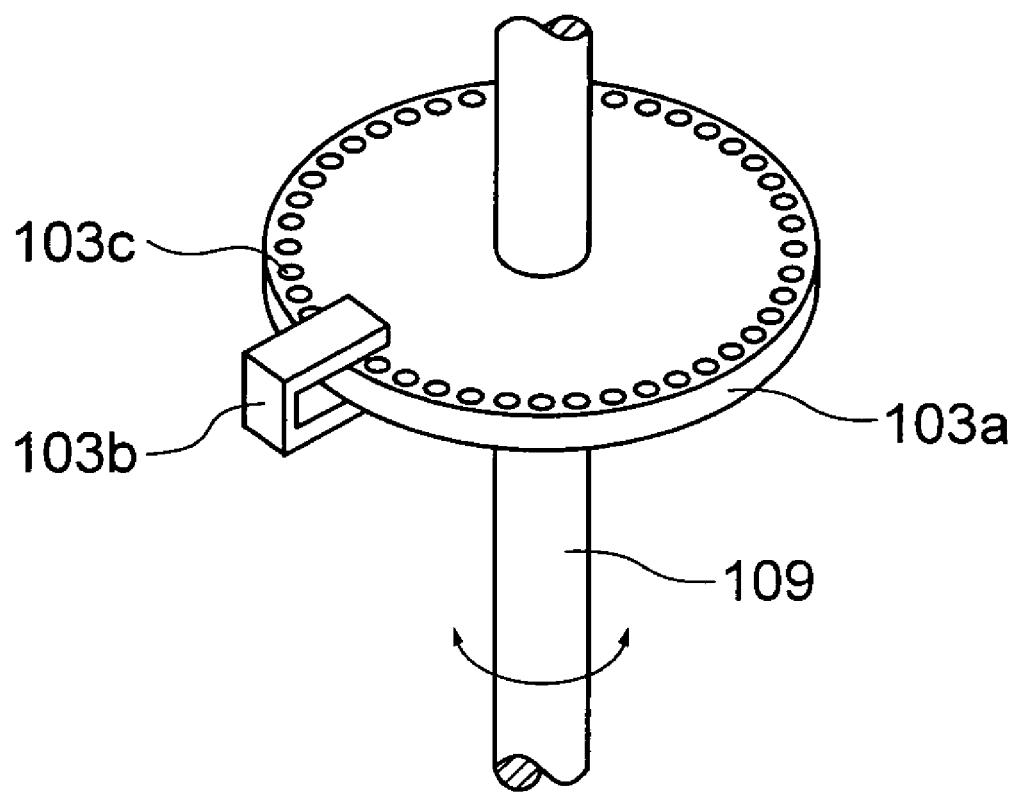
FIG. 6 is illustrative of the rotational angle detection mechanism of the prior-art example.
Figure 7A:
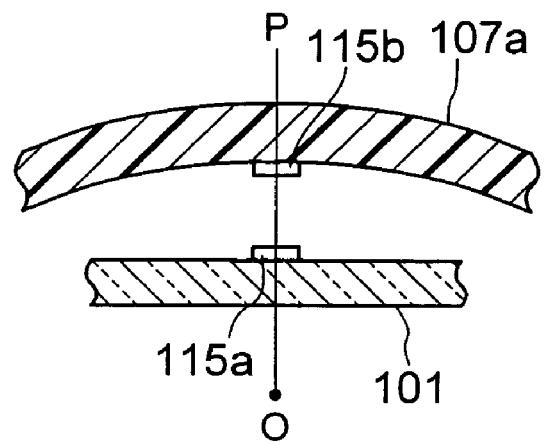
FIG. 7A shows a state in which the group of piezoelectric elements is at the reference position and FIG. 7B shows a state in which the group of piezoelectric elements 1 has rotated through θ° from the reference position.
Figure 7B:
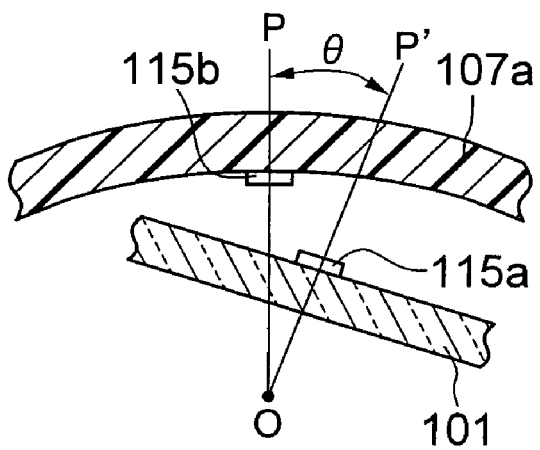

These operations set the group of piezoelectric elements 1 at the reference position at center front, as shown in FIG. 4A. Then the group of piezoelectric elements 1 is rotated and oscillated to left and right from the reference position by the rotational mechanism portion 2 that is linked to the stepping motor 10 and the control shaft 9, to send out and receive ultrasonic waves to and from the object to be detected. This ensures that a three-dimensional image can be obtained, from the relationships between predetermined positive or negative numbers of pulses and rotational angles. For example, the group of piezoelectric elements 1 could rotate to the right when the pulses are positive or to the left when the pulses are negative.

The above-described configuration makes it possible for the optical rotary plate 3a to oscillate and rotate, while being controlled within 90° in mutually opposite directions with reference to this boundary region P. The light detector 3d therefore senses either a blocked signal or a transmission signal, depending on the rotational position of the optical rotary plate 3a, so that rotating the optical rotary plate 3a either clockwise or counterclockwise in the predetermined manner will determine whether the boundary region P is present at one side or the other. It is therefore possible to detect the boundary region P reliably and determine the reference position of the group of piezoelectric elements 1 in a simple manner.

In addition, since the protective cover 19 is provided over the second bevel gear 8b, as shown in FIG. 1B, contact between the flexible substrate 5 and the second bevel gear 8b is prevented during the rotational oscillation of the group of piezoelectric elements 1. This makes it possible to prevent damage to the flexible substrate 5 and breakage of the conductive path 5a. In addition, since the flexible substrate 5 is folded flexibly on top of the protective cover 19, sufficient space can be ensured within the case 7 and thus the rotation and oscillation of the group of piezoelectric elements 1 can be done smoothly.

Figure 2B:
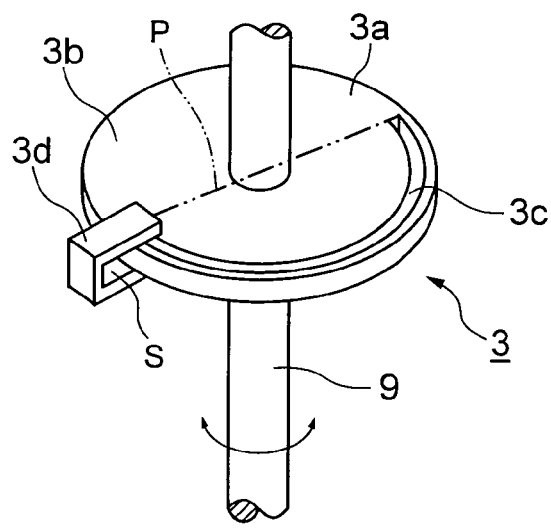

In the above-described embodying example, the optical rotary plate 3a is of a semicircular form, as shown in FIG. 2A, but since the rotational angle from the reference position (center front) of the group of piezoelectric elements 1 is, for example, within ±45° to ±90°, it is necessary to provide the light-blocking portion 3b and the light-transmitting portion 3c over a region of at least ±45°. In addition, the light-transmitting portion 3c could be such that the optical rotary plate 3a is a complete circle with an arc-shaped slit 3c provided around the outer periphery thereof as the light-transmitting portion, as shown in FIG. 2B. In essence, the configuration should be such that the light-blocking portion 3b and the light-transmitting portion 3c are formed in the optical rotary plate 3a in a continuous manner from the boundary region P.

Furthermore, the reference position of the group of piezoelectric elements 1 is described above as being the center front, but it could equally well be set as necessary, without being positioned such that the maximum rotational angle is formed to left and right, by way of example. Similarly, the protective cover 19 was described as being L-shaped, but it could equally well be of another shape in section, such as U-shaped. The connection between the control shaft 9 and the stepping motor 10 was described as being a gear linkage, but it could equally well be other linking means such as a belt and pulleys.

What is claimed is:

1. An ultrasonic probe comprising:
  a group of piezoelectric elements including a plurality of piezoelectric elements of a narrow card shape arrayed in a long-axis direction thereof and also connecting wires connected electrically to said piezoelectric elements and extending outward from at least one end side in a short-axis direction;
  a rotational mechanism portion that rotates and oscillates said group of piezoelectric elements in the short-axis direction about the center of said long-axis direction;
  a reference position detection sensor that detects a reference position of said group of piezoelectric elements in said short-axis direction; and
  a drive shaft and a stepping motor that are linked to said reference position detection sensor and drive said rotational mechanism portion;
  wherein an optical rotary plate for said reference position sensor, which has a boundary region between a light-blocking portion and a light-transmitting portion, is linked to said control shaft; said light-blocking portion and said light-transmitting portion are formed sequentially at a predetermined angle in mutually opposite directions from the center of said optical rotary plate, with reference to said boundary region, and also said optical rotary plate rotates no further than said predetermined angle with reference to said boundary region; said boundary region is detected by the transmission or blocking of light by said light-blocking portion and said light-transmitting portion; and thus the reference position of said group of piezoelectric elements is detected and set on the basis of said boundary region.

2. The ultrasonic probe as defined by claim 1, wherein said rotational mechanism portion is provided with a retaining plate that supports said group of piezoelectric elements on an upper surface thereof and has a leg portion on each side of a lower surface in said long-axis direction; a case of concave shape in which said leg portions connected to a peripheral wall thereof on either side of a line linking said two leg portions are freely rotatable and within which said connecting wires are sealed and is lead out to the exterior through a bottom wall thereof; a first bevel gear affixed to one inner surface of said leg portions and having teeth in an arc shape; a second bevel gear engaging with said first bevel gear and rotating in the horizontal plane; and said control shaft that rotatably supports said second bevel gear that is driven in rotation by said stepping motor and that is also sealed from said bottom wall and is lead out therefrom; wherein a protective cover that covers said second bevel gear is affixed to said bottom wall to prevent contact by said connecting wires on said second bevel gear.

3. An ultrasonic probe comprising at least:
  a group of piezoelectric elements including a plurality of piezoelectric elements of a narrow card shape arrayed in a long-axis direction and also connecting wires connected electrically to said piezoelectric elements and extending outward from at least one end side in a short-axis direction;
  a rotational mechanism portion that rotates and oscillates said group of piezoelectric elements in the short-axis direction about the center of said long-axis direction;
  a reference position detection sensor that detects a reference position in the short-axis direction of said group of piezoelectric elements; and
  a motor that is linked to said reference position detection sensor and that drives said rotational mechanism portion;
  wherein said rotational mechanism portion is provided with: a retaining plate that supports said group of piezoelectric elements on an upper surface thereof and has a leg portion on each side of a lower surface in said long-axis direction;

a case of concave shape in which said leg portions connected to a peripheral wall thereof on either side of a line linking said two leg portions are freely rotatable and within which flexible substrate is sealed and is lead out to the exterior through a bottom wall thereof;

a first bevel gear affixed to one inner surface of said leg portions and having teeth in an arc shape;

a second bevel gear engaging with said first bevel gear and rotating in the horizontal direction; and a control shaft that rotatably supports said second bevel gear that is driven in rotation by said stepping motor and that is also sealed from said bottom wall and is lead out therefrom;

and wherein a protective cover that covers said second bevel gear is affixed to said bottom wall to prevent contact by said connecting wires on said second bevel gear.

4. The ultrasonic probe as defined by claim 2, wherein the lateral section of said protective cover is L-shaped or U-shaped.

5. The ultrasonic probe as defined by claim 3, wherein the lateral section of said protective cover is L-shaped or U-shaped.

* * * * *